United States Patent [19]

Pari

[11] Patent Number: 5,801,235

[45] Date of Patent: Sep. 1, 1998

[54] OLIGONUCLEOTIDES WITH ANTI-CYTOMEGALOVIRUS ACTIVITY

[75] Inventor: Gregory S. Pari, North Smithfield, R.I.

[73] Assignee: Hybridon, Inc., Cambridge, Mass.

[21] Appl. No.: 249,386

[22] Filed: May 25, 1994

[51] Int. Cl.$^6$ ............... C07H 21/02; C07H 21/04; C12Q 1/68; C12N 5/16
[52] U.S. Cl. ............... 536/24.5; 435/6; 435/375; 536/24.3; 536/24.33
[58] Field of Search ............... 435/6, 948, 325, 435/375; 514/44; 536/23.1, 24.1, 24.3, 24.32, 24.5

[56] References Cited

U.S. PATENT DOCUMENTS

| | | | |
|---|---|---|---|
| 5,149,797 | 9/1992 | Pederson et al. | 536/23.1 |
| 5,149,798 | 9/1992 | Agrawal et al. | 536/25.3 |
| 5,194,428 | 3/1993 | Agrawal et al. | 514/44 |
| 5,242,906 | 9/1993 | Pagano et al. | 514/44 |
| 5,248,670 | 9/1993 | Draper et al. | 514/44 |
| 5,273,876 | 12/1993 | Hock et al. | 435/235.1 |
| 5,585,479 | 12/1996 | Hoke et al. | 536/24.5 |

FOREIGN PATENT DOCUMENTS

| | | |
|---|---|---|
| 0277773 | 8/1988 | European Pat. Off. |
| US91/05815 | 8/1991 | WIPO. |
| WO 95/28941 | 11/1995 | WIPO. |

OTHER PUBLICATIONS

Elek et al. (1974) *Lancet* 1:1–5.
Neff et al. (1979) *Proc. Soc. Exp. Biol. Med.* 160:32–27.
Froehler (1986) *Tetrahedron Lett.* 27:5575–5578.
Denzoit et al. (1986) *J. Immunol.* 89:271–277.
Caruthers et al. (1987) *Meth. Enzymol.* 154:287–313.
Agrawal et al. (1987) *Tetrahedron Lett.* 28:3539–3542.
Agrawal et al. (1988) *Proc. Natl. Acad. Sci.* (USA) 85:7079–7083.
Chee et al. (1990) *Curr. Top. Microbiol. Immunol.* 154:125–169.
Uhlmann et al. (1990) *Chem. Rev.* 90:543–584.
Babich et al. (1991) *Appl. Environ. Microbiol.* 57:2101–2103.
Tenney (1991) *Virol.* 182:199–210.
Agrawal in *Prospects for Antisense Nucleic Acid Therapy for Cancer and AIDS*, (Wickstrom, ed.) Liss, New York, (1991), pp. 145–148.
Agrawal (1992) *Trends Biotechnol.* 10:152–158.
Bergot et al. (1992) *J. Chromatog.* 559:35–42.
Pari et al. (1993) *J. Virol.* 67:2575–2582.
Pari et al. (1993) *J. Virol.* 67:6979–6988.
Azad et al. (1993) *Antimicrob. Agents Chemother.* 37:1945–1954.
Mocarski *Cytomegalogvirus Biology and Replication* (Raven Press, Ltd, New York), (1993) pp. 173–211.
Schooley in *Harrison's Principles of Internal Medicine* (13th Ed.) (Isselbacher et al., eds.) McGraw–Hill, Inc., New York, 1994, pp. 794–796.
Agrawal et al. in *Gene Regulation: Biology of Antisense RNA and DNA* (Erickson and Izant, eds.) Raven Press Ltd., New York 1992) pp. 273–283.
Sambrook et al. "Molecular cloning: A laboratory manual" 2nd. ed. Cold Spring Harbor Press, pp. 9.47–9.57, 11.4 and 11.46 1989.
He et al. "Characterization of human cytomegalovirus UL84 early gene and identification of its putative protein product" J. Virol. 66(2): 1098–1108 Feb. 1992.
Tenney et al. Human cytomegalovirus UL36–38 and US3 immediate–early genes: Temporally regulated expression of neclear, cytoplasmic, and polysome–associated transcripts during infection. J. Virol. 65(1): 6724–6734 Dec. 1991.
Wright et al. "Postranscriptional regulation of a class of human cytomegalovirus phosphoporteins encoded by an early transcription unit" J. Virol. 63(7): 3117–3127 Jul. 1989.

*Primary Examiner*—Nancy Degen
*Assistant Examiner*—Thomas G. Larson
*Attorney, Agent, or Firm*—Hale and Dorr LLP

[57] ABSTRACT

Disclosed are synthetic oligonucleotides 15 to 50 nucleotides in length which are specifically hybridizable with at least a portion of RNA or DNA derived from the UL36, UL84, UL101x-102, or UL112-113 genes of a cytomegalovirus. Also disclosed are pharmaceutical compositions including an oligonucleotide of the invention and methods of inhibiting cytomegalovirus infection using such oligonucleotides.

18 Claims, 12 Drawing Sheets

OLIGONUCLEOTIDES WITH ANTI-CYTOMEGALOVIRUS ACTIVITY

BACKGROUND OF THE INVENTION

This invention relates to cytomegalovirus infection. More particularly, this invention relates to the prevention and treatment of cytomegalovirus infection with antisense oligonucleotides.

Cytomegalovirus (CMV) is a member of the herpesvirus family which infects a wide range of animal species, including humans. Human CMV (HCMV) infects 50% to 80% of the population, ranging from mild or subclinical disease in immunocompetent adults, to severe morbidity in neonates and immunocompromised individuals such as transplant recipients and AIDS patients. In neonates, the infection may result in significant neurological defects, while in adults, severe mononucleosis, pneumonia, hepatitis, gastroenteritis, and sight-threatening chorioretinitis are common pathological symptoms. The virus is transmitted by repeated or prolonged intimate exposure, often through the ingestion of mother's milk or by sexual intercourse (Schooley in *Harrison's Principles of Internal Medicine* (13th Ed.) (Isselbacher et al., eds.) McGraw-Hill, Inc., New York, 1994, pp. 794–796).

CMVs have the structure typical of herpesviruses, including a double-stranded DNA genome encapsulated by an icosohedral capsid surrounded by lipoprotein membrane. The virus replicates in the cell nucleus and causes either lytic and productive or latent infection. Once infected, an individual probably carries the virus for life in the latent form unless T lymphocyte-mediated immunity is compromised. CMV also has the oncogenic ability to transform human and nonhuman cells and to stimulate their growth.

Prophylactic measures for preventing CMV infection have included the use of transplant tissue or blood from seronegative donors or blood that was frozen, thawed, and deglycerolized to decrease transfusion-associated transmission. Interferon alpha has been demonstrated to prevent reactivation CMV syndromes and to delay CMV excretion in high risk kidney transplant recipients (Schooley in *Harrison's Principles of Internal Medicine* (13th Ed.) (Isselbacher et al., eds.) McGraw-Hill, Inc., New York, 1994, pp. 794–796). Prophylactic acyclovir, a nucleoside analog, has been demonstrated to reduce CMV infection in seronegative renal transplant recipients.

Other attempts at preventive measures have included the development of anti-HCMV vaccines. However, vaccination did not protect fully against infection or reactivation of HCMV (EP 0 277 773; Elek et al. (1974) *Lancet* 1:1–5; Neff et al. (1979) *Proc. Soc. Exp. Biol. Med.* 160:32–37). U.S. Pat. No. 5,273,876 discloses another vaccine comprising an attenuated HCMV that includes a DNA sequence essential for the replication of HCMV and at least one foreign DNA sequence adapted for the expression of an antigenic polypeptide.

Therapeutic treatment of CMV has not yet proven to be very promising. Known antiviral drugs such as the nucleoside analogs acyclovir (acycloguanosine), and ara-A (adenine arabinoside) have had little effect on HCMV active infection. Ganciclovir [9-(1,2-dihydroxy-2-propoxymethyl guanine)]has been found to be an inhibitor of CMV polymerase after intracellular conversion to its triphosphate form. In AIDS patients also having CMV, continuous use of ganciclovir has controlled CMV infection. However, peripheral blood neutropenia and the development of ganciclovir-resistant strains are common in patients treated for more than three months.

Foscarnet (sodium phosphonoformate) has been used to treat HCMV infection (see, e.g., Azad et al. (1993) *Antimicrob. Agents Chemother.* 37:1945–1954). However, the disease recurs in treated individuals who are immunocompromised such as AIDS patients. In addition, foscarnet administration requires the use of an infusion pump and close clinical monitoring. Furthermore, drug toxicity from long term use and the emergence of resistant viral strains associated with long term therapy have limited the effectiveness of this compound (see, e.g., Azad et al., ibid.). Thus, limitations such as toxicity and resistance to known drugs demonstrate the need for new treatment strategies for CMV.

Recently, new chemotherapeutic agents have been developed which are capable of modulating cellular and foreign gene expression. These agents, called antisense oligonucleotides, bind to target single-stranded nucleic acid molecules according to the Watson-Crick or the Hoogsteen rule of base pairing, and in doing so, disrupt the function of the target by one of several mechanisms: by preventing the binding of factors required for normal transcription, splicing, or translation; by triggering the enzymatic destruction of mRNA by RNase H, or by destroying the target via reactive groups attached directly to the antisense oligonucleotide.

Antisense oligonucleotides have been used to inhibit the expression of a number of different viruses, including HIV-1, influenza, and other viruses (see, e.g., Agrawal et al., U.S. Pat. No. 5,194,428; Pederson et al., U.S. Pat. No. 5,149,797; Agrawal (1992) *Trends Biotechnol.* 10:152–158; Agrawal et al. in *Gene Regulation: Biology of Antisense RNA and DNA* (Erickson and Izant, eds.) Raven Press Ltd., New York (1992) pp. 273–283); Agrawal (1991) in *Prospects for Antisense Nucleic Acid Therapy for Cancer and AIDS*, (Wickstrom, ed.) Liss, New York, pp. 145–148).

Antisense oligodeoxynucleotides have also been designed to treat various herpesvirus infections. For example, oligonucleotides complementary to the EBNA-1 gene of Epstein-Barr virus (EBV) have been reported to inhibit EBV infection (U.S. Pat. No. 5,242,906). U.S. Pat. No. 5,248,670 discloses antisense oligonucleotides complementary to Herpes simplex virus type I genes UL13, UL39, and UL40 for the purpose of inhibiting the replication of virus in cultured HeLa cells.

In addition, antisense oligodeoxynucleotides have been designed to specifically treat CMV infection. For example, a phosphorothioate oligonucleotide complementary to the RNA of the HCMV major immediate-early region (IE2) has been shown to reduce the production of infectious virus in cultured human foreskin fibroblasts (Azad et al. (1993) *Antimicrob. Agents Chemother.* 37:1945–1954). (The nucleotide sequence coordinates (i.e., nomenclature) are from the published DNA sequence data of Chee et al. (*Curr. Top. Microbiol. Immunol.* (1990) 154:125–169). The IE2 region encodes several proteins which regulate viral gene expression.

PCT/US 91/05815 discloses oligonucleotides which are complementary to portions of CMV mRNAs which code for the IE1, IE2, or DNA polymerase (UL54) proteins, including at least a portion of the mRNA cap site, the AUG region, the conserved amino acid region, the CMV insertion regions between particular bases of the DNA polymerase gene, an intron/exon junction region of the IE1 or IE2 gene, or a nuclear location signal region of the IE2 gene.

However, a need for new strategies still remains for the treatment and prevention of HCMV infections. In particular, compositions and therapeutic methods utilizing these compositions are desired which are effective at low concentrations, for long periods of time, and whose use are accompanied by little or no cellular toxicity.

In addition, there is a need for CMV strains having mutations in essential genes for the study of the genetics of this virus. Unfortunately, no one has succeeded in creating such mutant strains, thus impeding the study of the genetics of this important virus.

SUMMARY OF THE INVENTION

It has been discovered that inhibiting the expression of certain HCMV genes not heretofore identified as being required for viral DNA replication does indeed inhibit viral DNA expression. This unexpected finding has been exploited to develop the present invention which provides synthetic oligonucleotides that inhibit HCMV DNA replication. These oligonucleotides hybridize under normal physiological conditions to specific portions of the cytomegalovirus genome or to the transcripts thereof, thereby inhibiting their expression.

As used herein, the term "synthetic oligonucleotide" includes artificially synthesized (i.e., not made by a DNA or RNA polymerase in a cell) polymers of 5 to 50 and preferably from about 15 to about 30 ribonucleotide and/or deoxyribonucleotide monomers connected together or linked by at least one 5' to 3' internucleotide linkage.

In preferred embodiments, the synthetic oligonucleotides of the invention are specifically hybridizable with at least a portion of RNA or DNA derived from the UL36, UL84, UL101x-102, or UL112-113 genes of a cytomegalovirus. These particular genes were not known heretofore to be required for viral DNA replication.

In specific embodiments of the invention, the oligonucleotides are hybridizable with at least a portion of an intron/exon boundary of UL36 or UL112-113, of the putative translational start region or the 5' untranslated region of UL101x, or the putative translational start region of UL84 RNA or the DNA sequence encoding this transitional start region.

As used herein "UL101x" refers to a small open reading frame (ORF) upstream of the UL102 ORF. UL101x and UL102 comprise a region (the "UL101x-102" region) which most likely encodes the primase associated factor of the helicase-primase complex.

In certain preferred embodiments of the invention, the oligonucleotides (UL36 I/X 1, UL36 I/X 1A, UL36 I/X 1C) targeting the intron-exon regions of UL36 have the nucleotide sequences set forth in the Sequence Listing as SEQ ID NOS:1-3. In another preferred embodiment, the oligonucleotides (UL84a and UL85b) targeting the 5'-untranslated region of UL84 have the nucleotide sequence set forth as SEQ ID NOS:4 and 5. In yet another preferred embodiment, the oligonucleotide targeting the putative translational start region (UL101x a) has the nucleotide sequences set forth as SEQ ID NO:6. In an additional preferred embodiment, the oligonucleotides targeting the intron/exon boundaries of the UL112-113 region have the nucleotide sequences set forth as SEQ ID NOS:7-9.

In certain preferred embodiments of the invention, the oligonucleotides are modified. The term "modified oligonucleotide" is used herein as an oligonucleotide in which at least two of its nucleotides are covalently linked via a synthetic linkage, i.e., a linkage other than a phosphodiester between the 5' end of one nucleotide and the 3' end of another nucleotide in which the 5' nucleotide phosphate has been replaced with any number of chemical groups. Preferable synthetic linkages include alkylphosphonates, phosphorothioates, phosphorodithioates, alkylphosphonothioates, phosphoramidates, phosphoramidites, phosphate esters, carbamates, carbonates, phosphate triesters, acetamidate, and carboxymethyl esters. In one preferred embodiment of the invention, the oligonucleotide comprises at least one phosphodiester, phosphorothioate, methylphosphonate, or phosphoramidite linkage or a combination of such linkages located anywhere in the oligonucleotide structure.

The term "modified oligonucleotide" also encompasses oligonucleotides with a modified base and/or sugar. For example, a 3',5'-substituted oligonucleotide is a modified oligonucleotide having a sugar which, at both its 3' and 5' positions is attached to a chemical group other than a hydroxyl group (at its 3' position) and other than a phosphate group (at its 5' position). A modified oligonucleotide may also be a capped species. In addition, unoxidized or partially oxidized oligonucleotides having a substitution in one non-bridging oxygen per nucleotide in the molecule are also considered to be modified oligonucleotides. Also considered as modified oligonucleotides are oligonucleotides having nuclease resistance-conferring bulky substituents at their 3' and/or 5' end(s) and/or various other structural modifications not found in vivo without human intervention are also considered herein as modified.

The oligonucleotides of the invention hybridize to the cytomegalovirus DNA or RNA under normal physiological conditions existing within a cell harboring the cytomegalovirus DNA or RNA. Such conditions include pH, temperature, and ionic conditions.

In some aspects, the invention provides an oligonucleotide which has antiviral activity against cytomegalovirus effected by hybridization with a portion of the viral DNA or RNA. A pharmaceutical composition including at least one of the oligonucleotides of the invention, and in some embodiments, at least two different oligonucleotides of the invention, and a pharmaceutically acceptable carrier, are provided.

The pharmaceutical composition is used in a method of inhibiting, preventing, and/or reducing HCMV replication in a cell. In this method, a therapeutic amount of the pharmaceutical composition is administered to the cell which is to be protected from infection or treated for an existing infection. The oligonucleotide (or oligonucleotides) in the pharmaceutical composition enters the cell, wherein it (they) hybridize(s) to CMV DNA or RNA, thereby inhibiting CMV replication. The prophylactic aspect of the method can be used in healthy individuals at risk for CMV infection. It can also be used to prevent inadvertent CMV contamination of cell lines in a laboratory in which CMV is being used. The pharmaceutical composition is also utilized in a method of treating HCMV infection wherein the composition is administered to an infected mammal or cell.

The invention also provides a method of making the epigenetic equivalent of a mutant DNA replication-deficient cytomegalovirus. In this method, an oligonucleotide complementary to the UL36, UL84, or UL101x-102 genes of CMV are administered to a CMV-infected cell. CMV infection will progress to the point at which the function or protein encoded by the gene or transcript to which the oligonucleotide has hybridized is required for DNA replication, thereby resulting in a mutant CMV. This method will allow genetic study of CMV in the absence of mutant strains, which have thus far been largely unavailable.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

The genome of HCMV consists of double-stranded linear DNA which is about 240,000 nucleotides in length and has a potential to encode about 200 genes. Expression of CMV genes in a permissive cell or one capable of being infected by the virus is regulated by a cascade of events divided into three phases: the immediate early (IE), early (E), and late (L) periods. After adsorption, penetration, and uncoating of the virus, the linear HCMV genome is thought to circularize and then to replicate in the nucleus by a mechanism producing concatemeric products which are subsequently cleaved and packaged during virus assembly. IE mRNAs are synthesized within 1 to 4 hours of the adsorption, penetration, and uncoating of the virus. The protein products of these transcripts are involved in the initiation of early transcriptional events. E proteins, like IE proteins, are encoded by mRNAs transcribed prior to viral DNA synthesis. Some of these E proteins play a role in nucleotide metabolism and DNA synthesis in the infected cell. The transcription of L mRNAs is at its peak after the onset of DNA synthesis. These mRNAs encode constituents of the viral envelope, capsid proteins, and other proteins required for viral assembly, structural integrity, and release of the mature virion from the infected cell.

HCMV contains one origin of lytic-phase replication called oriLyt. This is a cis acting element known to direct DNA replication in an artificial, in vitro, virus free, cotransfection-replication assay. Genes demonstrated to be required for oriLyt-dependent viral DNA replication include UL54 (DNA polymerase), UL44 (polymerase accessory protein), UL57 (a single-stranded DNA binding protein), UL105, UL70, UL101x-UL102 (proposed subunits of a helicase-primase complex), UL36-38 (regulatory protein, general transcriptional activator), irs1 (or TRS1) (regulatory protein, activator of gene expression), IE1/IE2 (regulatory protein), as well as UL84 (early temporal class nucleus-associated protein with unknown function) and UL112-113 (early temporal class nucleus-associated proteins with unknown function), which have not previously been implicated either in HCMV DNA replication or in the regulation of gene expression (Pari et al. (1993) *J. Virol.* 67:2575–2582; Pari et al. (1993) *J. Virol.* 67:6979–6988).

It has been discovered that treatment of cells with oligonucleotides directed to specific regions of the HCMV genome results in the inhibition of HCMV DNA replication. In particular, oligonucleotides complementary to transcripts or DNA of the UL36, UL84, UL101x-102, and UL112-113 genes are able to inhibit HCMV DNA replication in infected cells. These targeted genes encode early temporal class nucleus-associated proteins, some of which having unknown function (UL84, UL112-113). All of these genes are among those known to be required for transient complementation of HCMV oriLyt-dependent DNA replication, an artificial system set up for a cotransfection-replication assay.

Figure 1:
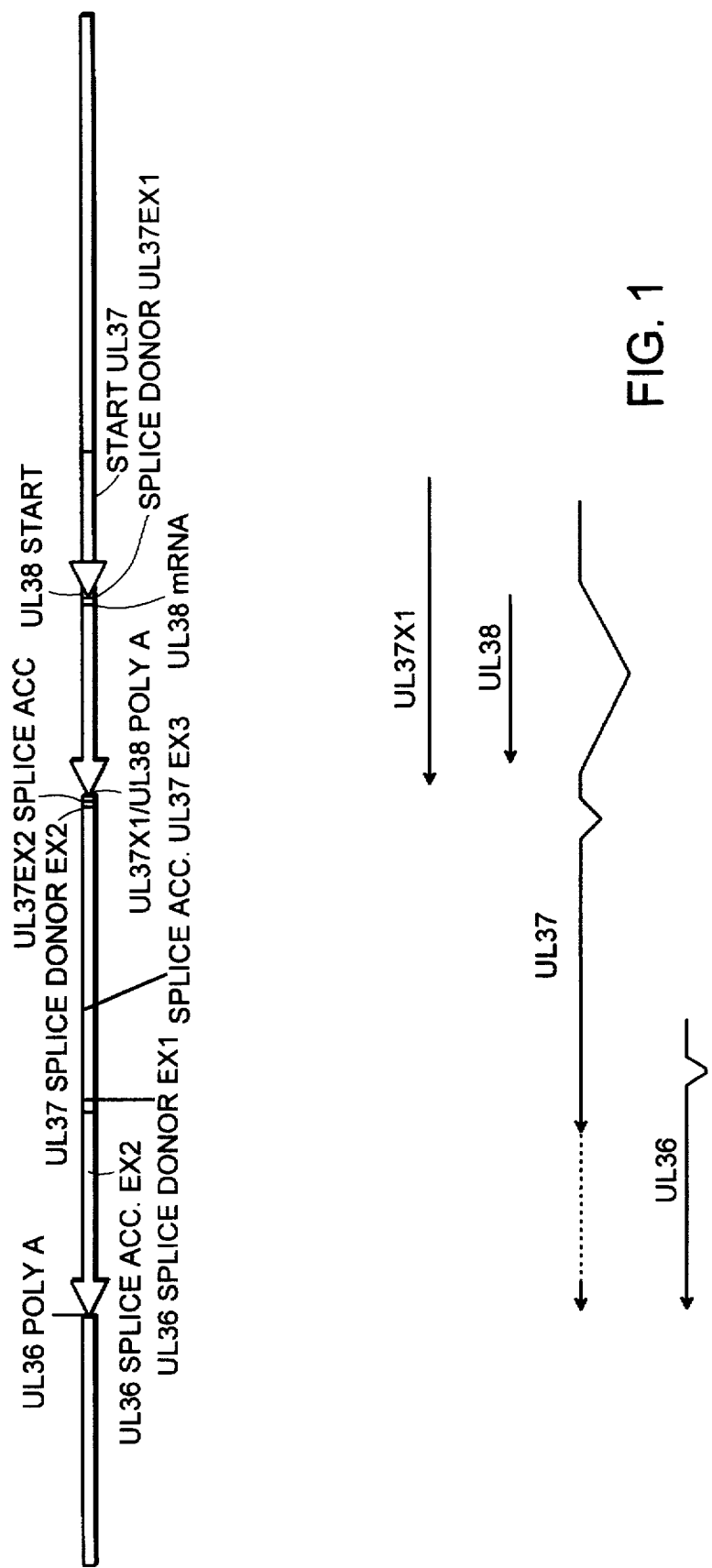
FIG. 1 is a schematic representation of the UL36-38 region of the HCMV genome showing the transcripts from this region.

Unexpectedly, it has been discovered that the UL36, UL84, and UL101x-102 genes are also required for HCMV DNA replication. Thus, the invention includes oligonucleotides targeted to these genes. In specific embodiments, the oligonucleotide is targeted to the intron-exon boundary of UL36, an immediate early protein present at all times during the infectious cycle. A genomic map of the UL36-38 region, as well as transcripts targeted by the oligonucleotides of the invention, are shown in FIG. 1. Representative oligonucleotides of this type (UL36 I/X 1, UL36 I/X 1A, and UL36 I/X 1C) have the nucleotide sequences set forth in Table 1 below and in the Sequence Listing as SEQ ID NO:1, SEQ ID NO:2, and SEQ ID NO:3.

Figure 2:
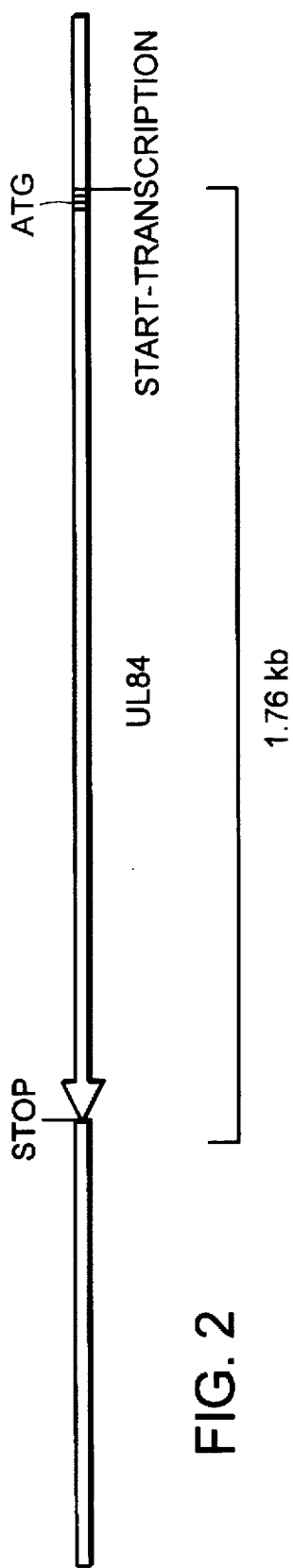
FIG. 2 is a schematic representation of the UL84 region of the HCMV genome.
Figure 3:
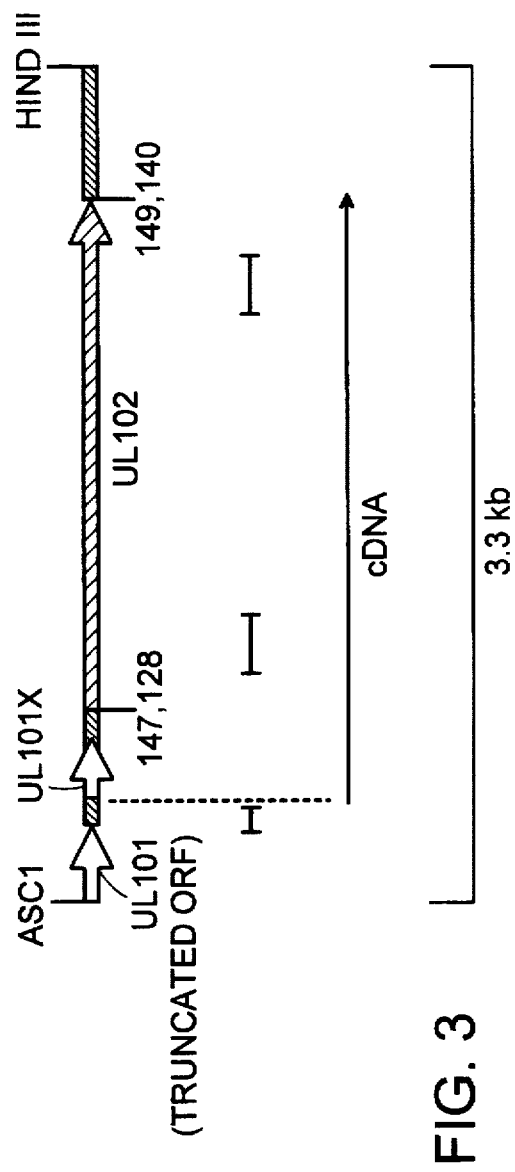
FIG. 3 is a schematic representation of the UL101x and UL102 (primase associated factor) region of the HCMV genome.

Oligonucleotides of the invention specific for other regions of the HCMV genome include those complementary to the UL84 or UL101x DNA or transcript(s) including the putative translational start region. This region in UL84 can be seen in FIG. 2. Representative oligonucleotides (UL84a and UL84 b) directed to UL84 have the nucleotide sequences set forth in TABLE 1 and in the Sequence Listing as SEQ ID NOS:4 and 5. FIG. 3 shows the putative translational start region of the UL101x-102 loci. A representative oligonucleotides (UL101x a) directed to a UL101x transcript has the nucleotide sequence set forth in TABLE 1 and in the Sequence Listing as SEQ ID NO:6. The efficiency of these oligonucleotides is surprising, because the prior art teaches that it is the UL102 open reading frame (ORF) that is required for replication and that its encoded polypeptide is translated from the UL102 ATG. Here, it is demonstrated that oligonucleotides directed against the upstream 101x ATG are effective. Moreover, oligonucleotides directed against the putative UL102 ATG were ineffective.

Figure 4:
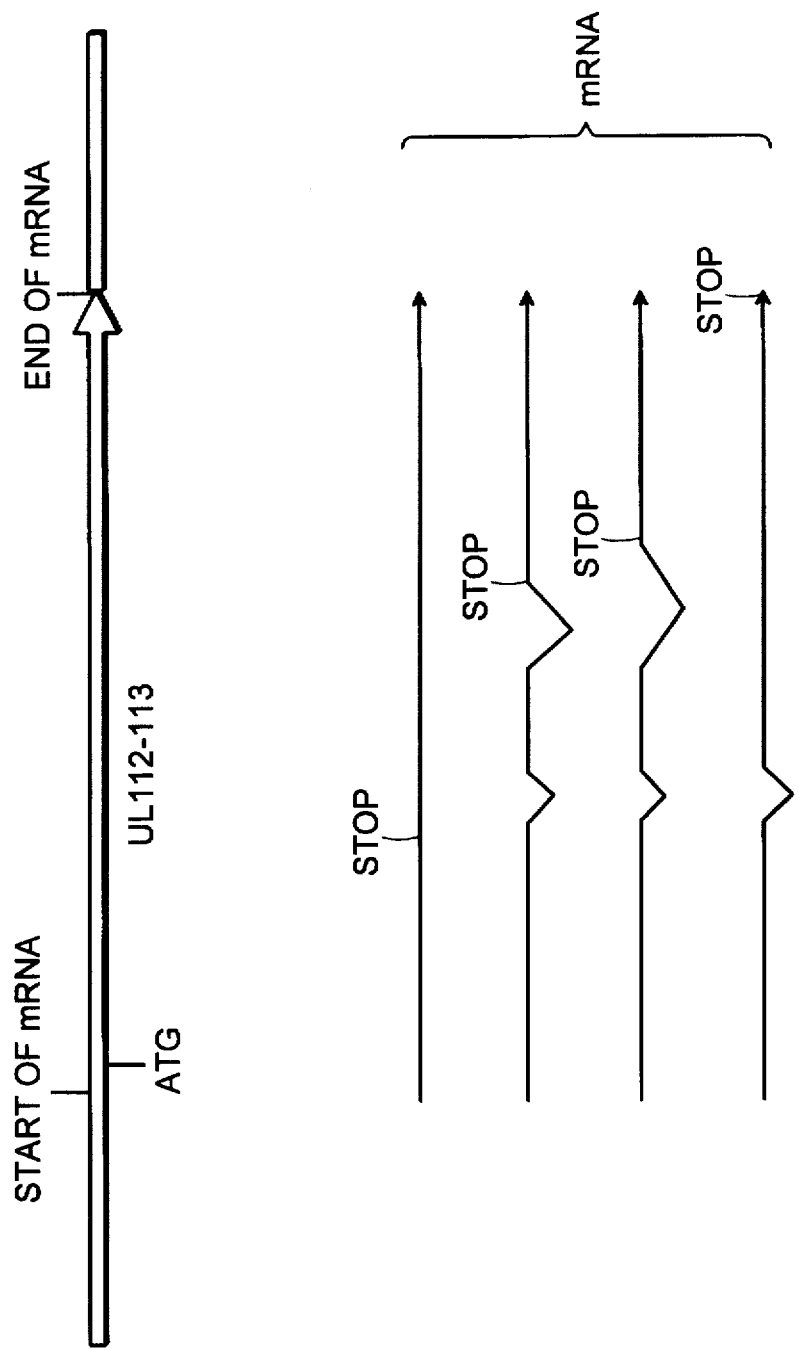
FIG. 4 is a schematic representation of the UL112-113 region of the HCMV genome showing regions targeted by oligonucleotides of the invention.
Figure 5:
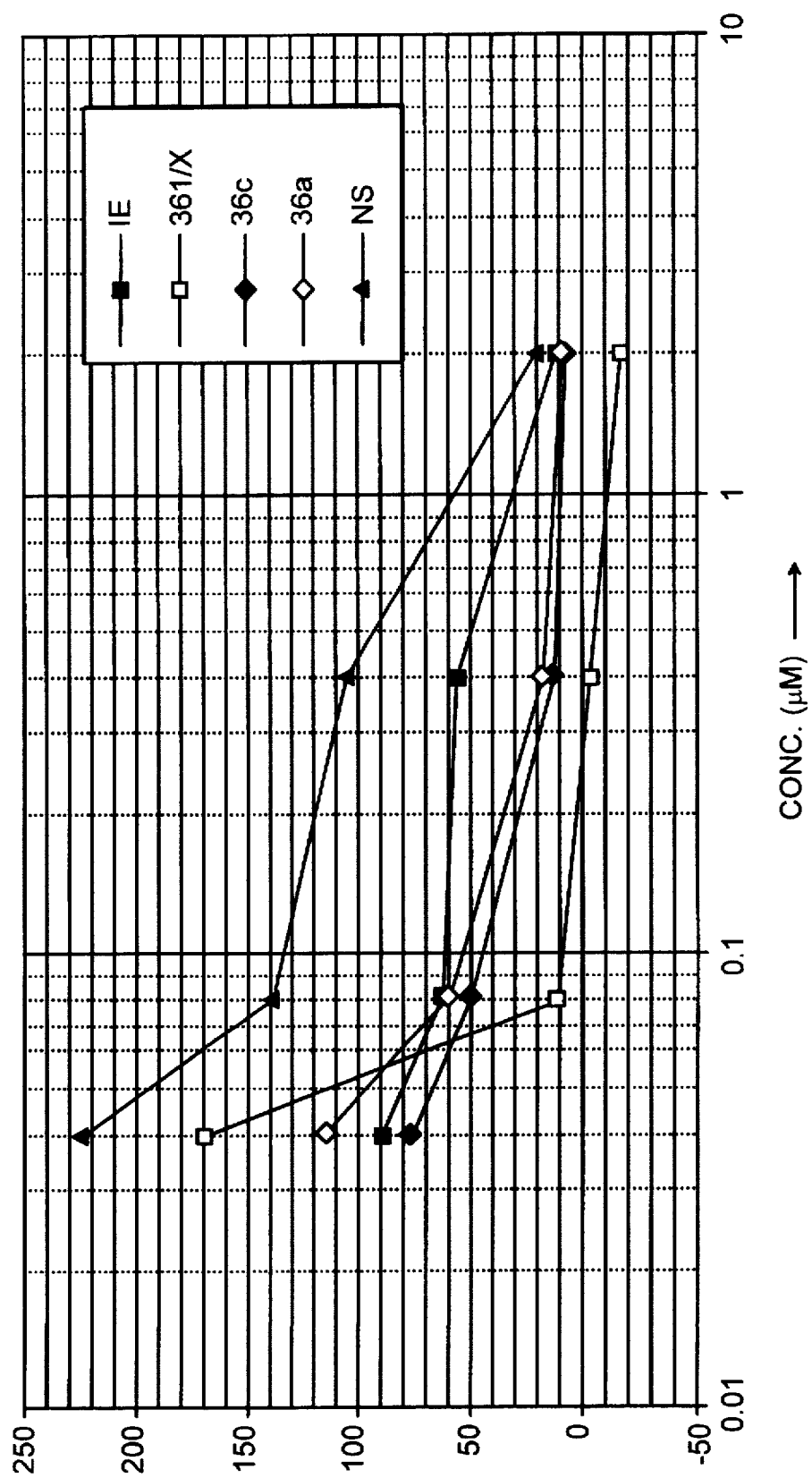
FIG. 5 is a graphic representation of the results of an ELISA in which cells preincubated with oligonucleotides complementary to IE, UL36 I/X 1, UL36c (UL36 I/X 1C), UL36a (UL36 I/X 1 A), and NS (nonspecific oligonucleotide) were infected with HCMV (MOI=0.4), incubated for 6 days, and then immunostained for viral UL44 protein.

Another portion of the HCMV genome to which oligonucleotides of the invention are targeted includes the UL112-113 complex spliced region. In particular, the intron-exon boundaries of this region, shown schematically in FIG. 4, have been targeted. Representative oligonucleotides (UL112-113I/X 1, UL112-113 I/X 2, UL112-113 I/X 3) directed to this region have the nucleotide sequence listed below in Table 1 and as set forth in the Sequence Listing as SEQ ID NOS:7-9.

TABLE 1

| gene targeted | oligonucleotide sequence 5' —————— 3' | SEQ ID NO: |
|---|---|---|
| UL36 I/X 1 | TGGGGCTTACCTTGCGAACA | 1 |
| UL36 I/X 1A | GACGTGGGGCTTACCTTGCG | 2 |
| UL36 I/X 1C | TCTTCAACGACGTGGGGCTT | 3 |
| UL84a | GACGCGTGGCATGCTTGGTGT | 4 |
| UL84b | AGGTTGGGGTCGACGCGTGGC | 5 |
| UL101x a | GGCTGAGCGGTCATCCTCGGA | 6 |
| UL112-113 I/X 1 | CGGGACTCACCGTCGTTCTG | 7 |
| UL112-113 I/X 2 | GGAGGAGAGCCTACAGACGG | 8 |
| UL112-113 I/X 3 | AGTAACGCACCGTCGGTGCC | 9 |

Oligonucleotides of the invention are composed of deoxyribonucleotides, ribonucleotides, 2'-O-methylribonucleotides, or any combination thereof, with the 5' end of one nucleotide and the 3' end of another nucleotide being covalently linked. These oligonucleotides are at least 6 nucleotides in length, but are preferably 15 to 50 nucleotides long, with 15 to 30 mers being the most common. These oligonucleotides can be prepared by art recognized methods. For example, nucleotides can be covalently linked using art-recognized techniques such as phosphoramidate, H-phosphonate chemistry, or methylphosphoramidate chemistry (see, e.g., Uhlmann et al. (1990) Chem. Rev. 90:543–584; Agrawal et al. (1987) Tetrahedron. Lett. 28: (31) :3539–3542); Caruthers et al. (1987) Meth. Enzymol. 154:287–313; U.S. Pat. No. 5,149,798) which can be carried out manually or by an automated synthesizer and then processed (reviewed in Agrawal et al. (1992) Trends Biotechnol. 10:152–158).

The oligonucleotides of the invention may also be modified in a number of ways without compromising their ability to hybridize to HCMV DNA or mRNA. For example, the oligonucleotides may contain other than phosphodiester internucleotide linkages between the 5' end of one nucleotide and the 3' end of another nucleotide in which the 5' nucleotide phosphate has been replaced with any number of chemical groups. For example, oligonucleotides with phosphorothioate linkages can be prepared using methods well known in the field such as methoxyphosphoramidite (see, e.g., Agrawal et al. (1988) Proc. Natl. Acad. Sci. (U.S.A.) 85:7079–7083) or H-phosphonate (see, e.g., Froeher (1986) Tetrahedron Lett. 27:5575–5578) chemistry. The synthetic methods described in Bergot et al. (J. Chromatog. (1992) 559:35–42) can also be used. Examples of other chemical groups include alkylphosphonates, phosphorodithioates, alkylphosphonothioates, phosphoramidates, phosphoramidites, phosphate esters, carbamates, acetamidate, carboxymethyl esters, carbonates, and phosphate triesters. oligonucleotides with these linkages can be prepared according to known methods (see, e.g., Agrawal and Goodchild (Tetrahedron Lett. (1987) 28:3539–3542; Agrawal et al. (Proc. Natl. Acad. Sci. (U.S.A.) (1988) 85:7079–7083); Uhlmann et al. (Chem. Rev. (1990) 90:534–583; and Agrawal et al. (Trends Biotechnol. (1992) 10:152–158).

Other modifications include those which are internal or are at the end (s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3',5'-substituted oligonucleotide having a sugar which, at both its 3' and 5' positions is attached to a chemical group other than a hydroxyl group (at its 3' position) and other than a phosphate group (at its 5' position). Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule (reviewed in Agrawal et al. (1992) Trends Biotechnol. 10:152-158).

To assess the antiviral effect of individual oligonucleotides of the invention, an ELISA assay was performed. Briefly, cell susceptible to HCMV infection (i.e., permissive cells) were pretreated with varying concentrations of the oligonucleotides listed in TABLES 2A and 2B.

TABLE 2A

| Oligo | Directed to |
|---|---|
| UL36 I/X 1 | first I/X boundary |
| UL36 I/X 1A | IE intron/exon boundary |

TABLE 2A-continued

| Oligo | Directed to |
| --- | --- |
| UL36 I/X 1B | IE intron/exon boundary |
| UL36 I/X 1C | IE intron/exon boundary |
| UL37 I/X 1 | IE 1st intron/exon boundary |
| UL37 I/X 2 | IE 2d intron/exon boundary |
| UL37 I/X 3 | IE 3rd intron/exon boundary |
| UL44a | E polymerase processivity factor |
| UL44b | E polymerase processivity factor |
| UL70a | E helicase-primase complex |
| UL70b | E helicase-primase complex |
| UL84a | E putative translational start |
| UL84b | E putative translational start |
| UL101x a | primase associated factor (PAF) |
| UL102a | PAF |
| UL102b | PAF |
| UL112-113 I/X 1 | E intron/exon boundary |
| UL112-113 I/X 2 | E intron/exon boundary |
| UL112-113 I/X 3 | E intron/exon boundary |
| irs1a | IE putative translational start |
| irs1b | IE putative translational start |
| orila | origin of replication |
| orilb | origin of replication |
| IE (ISIS) | 1E2 translational start |

TABLE 2B

| Oligo | Sequence | SEQ ID NO: |
| --- | --- | --- |
| UL36 I/X 1 | TGGGGCTTACCTTGCGAACA | 1 |
| UL36 I/X 1A | GACGTGGGGCTTACCTTGCG | 2 |
| UL36 I/X 1B | CAACGACGTGGGGCTTACCT | 10 |
| UL36 I/X 1C | TCTTCAACGACGTGGGGCTT | 3 |
| UL37 I/X 1 | ACCCCTGCTTACTGGTGAGA | 11 |
| UL37 I/X 2 | GTTGTTTTTACCTGAAACCC | 12 |
| UL37 I/X 3 | CCGAACGGCGGTTTCTCCAC | 13 |
| UL44a | CTTGCGATCCATCCCGGACAG | 14 |
| UL44b | CTCCGAGAGGCGCGTCTTGC | 15 |
| UL70a | ACGAGCGTCATCGTCGCGCCGG | 16 |
| UL70b | CATCGTCGCGCCGGCACGATGC | 17 |
| UL84a | GACGCGTGGCATGCTTGGTGT | 4 |
| UL84b | AGGTTGGGGTCGACGCGTGGC | 5 |
| UL101x a | GGCTGAGCGGTCATCCTCGGA | 6 |
| UL102a | GCGAAACGACATGGCCAAATC | 18 |
| UL102b | GCGCGTGGGTGCCATACTCTT | 19 |
| UL112-113 I/X 1 | CGGGACTCACCGTCGTTCTG | 7 |
| UL112-113 I/X 2 | GGAGGAGAGCCTACAGACGG | 8 |
| UL112-113 I/X 3 | AGTAACGCACCGTCGGTGCC | 9 |
| irs1a | CCGTTGCGCTGGGCCATGGG | 20 |
| irs1b | CATGGGCGCCGGACACCTGC | 21 |
| orila | AAATCATCTCTGACGTAGCG | 22 |
| orilb | GCTCGCTACGCTCGCTACGTC | 23 |
| IE (ISIS) | GCGTTTGCTCTTCTTCTTGCG | 24 |

The cells were then infected with HCMV at a multiplicity of infection (MOI) ranging from 0.05 to 0.4. After an incubation period, HCMV replication was measured in an indirect manner by determining the relative level of UL44, an HCMV protein required for DNA replication, present in the infected cells. A lower level of UL44 is detected when HCMV replication is suppressed.

The results in FIGS. 5–7 and 9 demonstrate that an antisense oligonucleotide directed against UL36suppresses the production of the UL44 gene product to a much greater extent than any other antisense oligonucleotide tested in these experiments. As described above, oligonucleotides directed to this gene are complementary to the intron-exon boundary of the unspliced UL36 RNA. Representative oligonucleotides include UL36 I/X 1 which has the nucleotide sequence set forth in the Sequence Listing as SEQ ID NO:1, UL36 I/X 1A (SEQ ID NO:2), and UL36 I/X 1C (SEQ ID NO:3).

Figure 6:
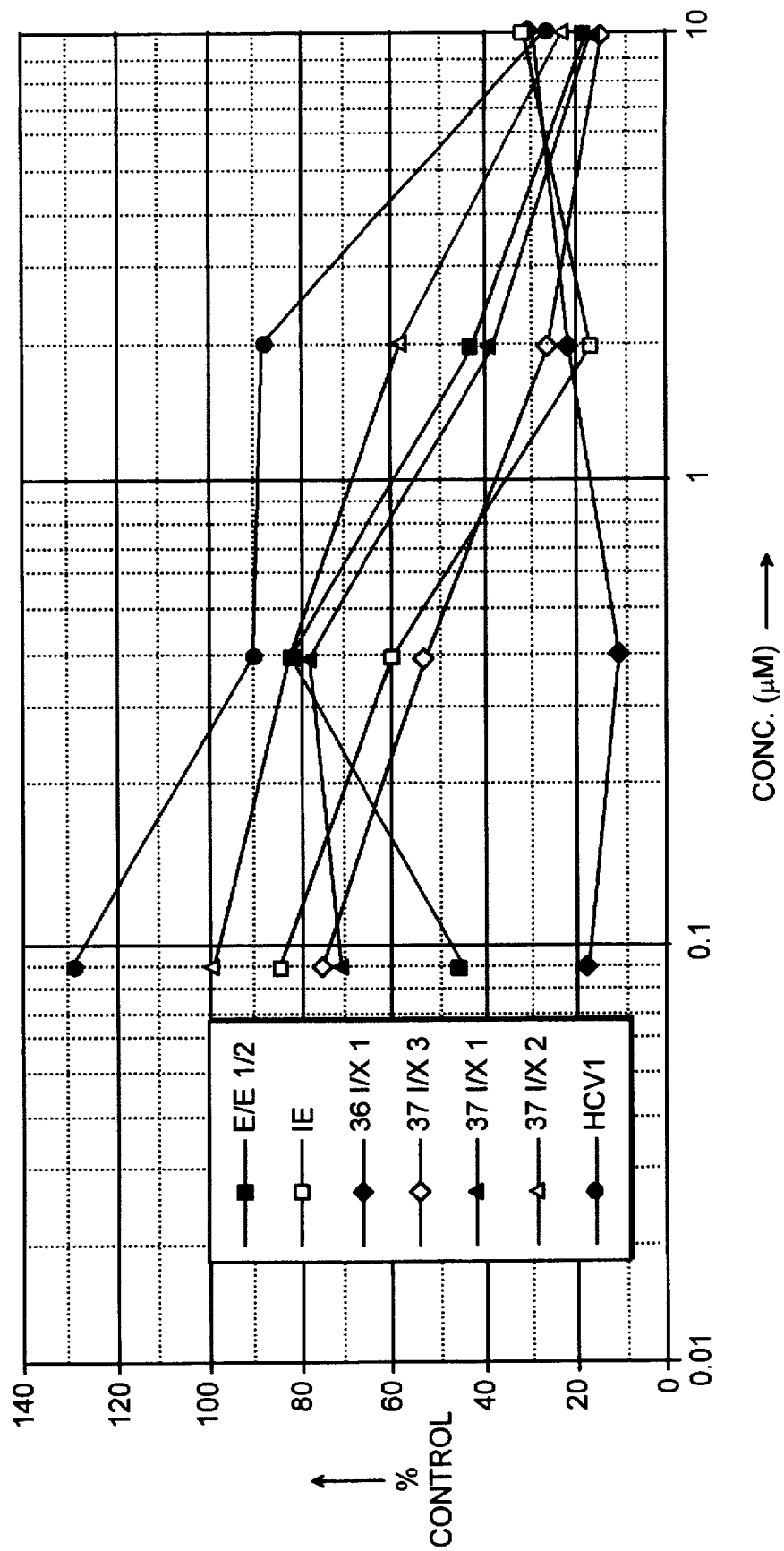
FIG. 6 is a graphic representation of the results of an ELISA in which cells preincubated with oligonucleotides complementary to E/E 1/2, IE, UL36 I/X 1, UL37 I/X 3, UL37 I/X 1, UL37 I/X 2, and HCV1 were infected with HCMV (MOI=0.05), incubated for 5 days, and then immunostained for viral UL44 protein.

FIG. 6 shows the results of a similar experiment wherein oligonucleotides directed against other loci within the UL36-38 region (i.e., UL37) were used in addition to the UL36 I/X 1oligonucleotide. Oligonucleotides directed to these other loci shown little if any inhibitory activity.

Figure 7:
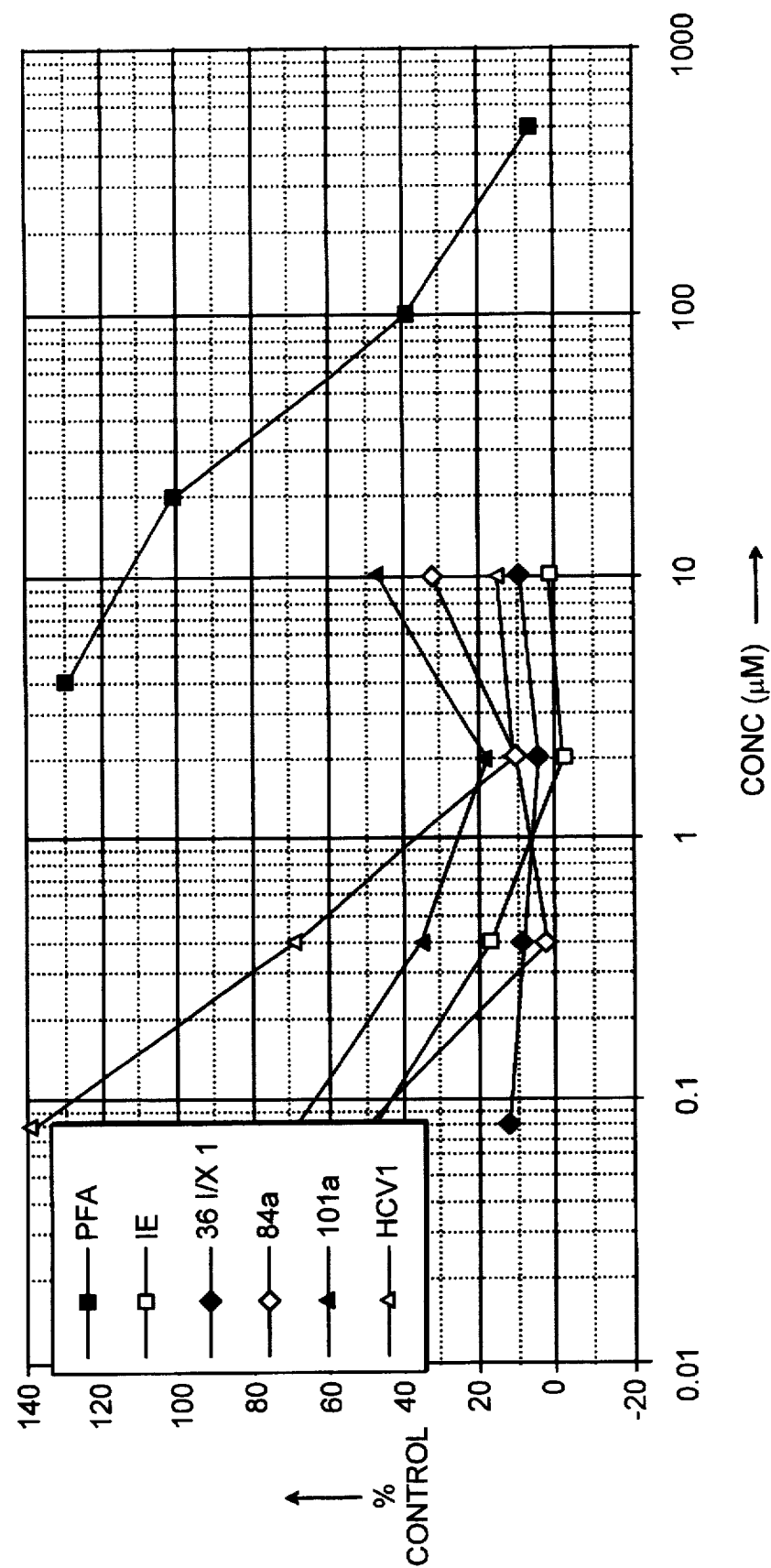
FIG. 7 is a graphic representation of the results of an ELISA in which cells preincubated with oligonucleotides complementary to IE, UL36 I/X 1, UL84a, UL101a, or HCV1, or with phosphonoformic acid (pfa), were infected with HCMV (MOI=0.05), incubated for 6 days, and then immunostained for viral UL44 protein.
Figure 11:
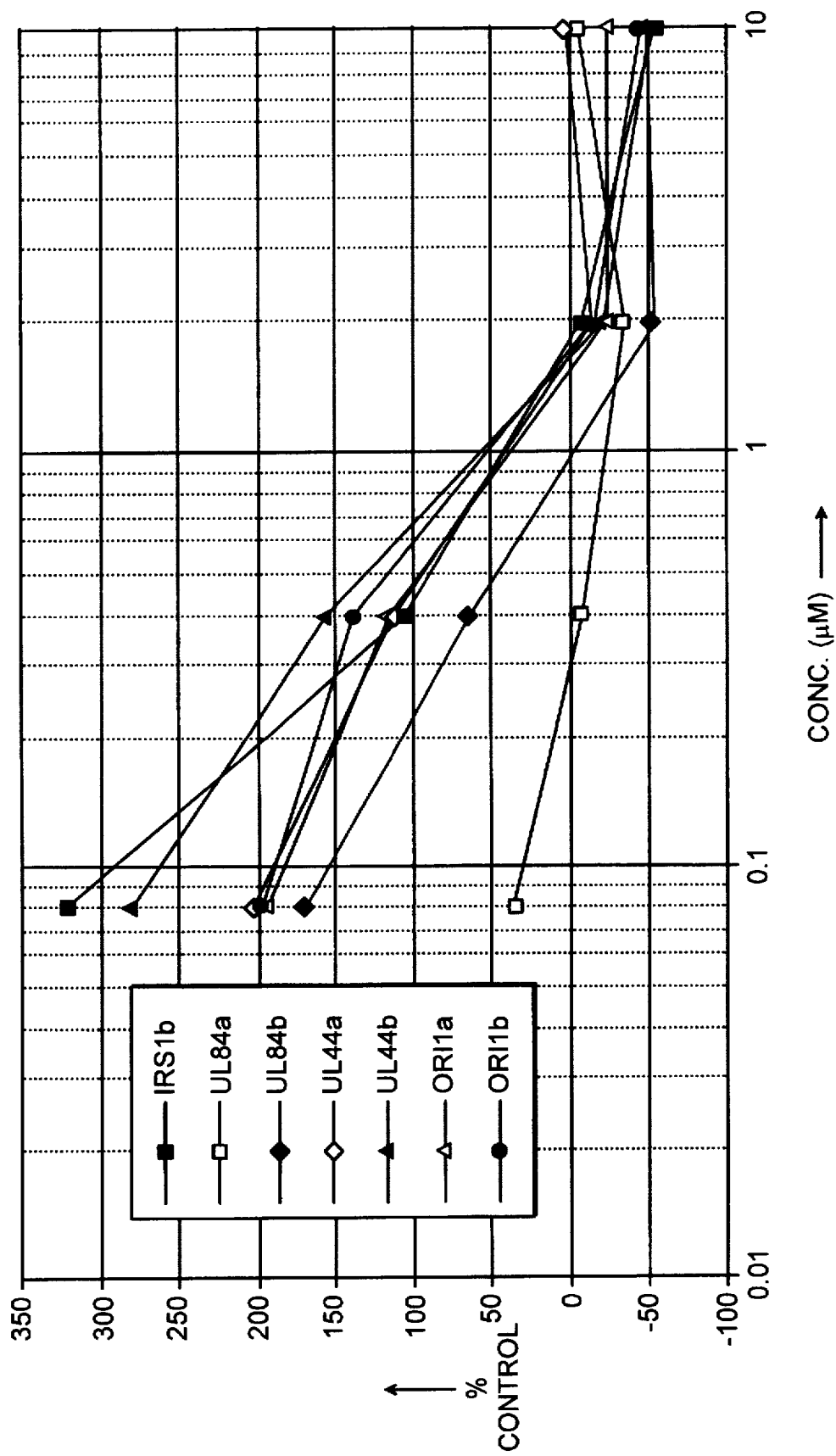
FIG. 11 is a graphic representation of the results of an ELISA in which cells preincubated with oligonucleotides complementary to irslb, UL84a, UL84b, UL44a, UL44b, orila, and orilb were infected with HCMV (MOI=0.05), incubated for 5 days, and then stained for viral UL44 protein.

FIGS. 7 (as well as FIGS. 8 and 11) also demonstrate the inhibitory effect of oligonucleotides directed to the UL84 transcript or gene: UL84a has a nucleotide sequence set forth in the Sequence Listing as SEQ ID NO:4, and UL84b has a nucleotide sequence set forth in the Sequence Listing as SEQ ID NO:5.

Figure 8:
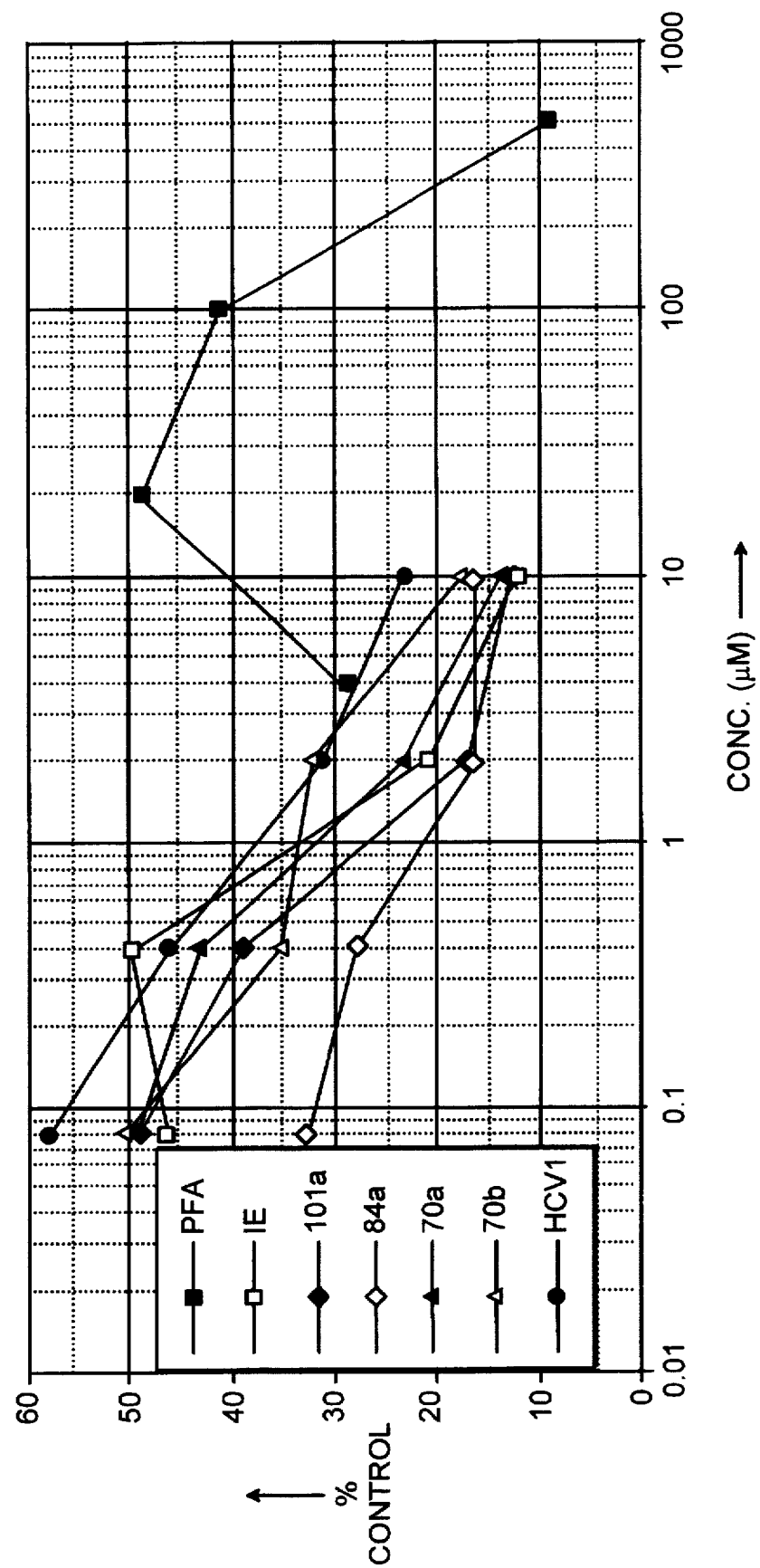
FIG. 8 is a graphic representation of the results of an ELISA in which cells preincubated with oligonucleotides complementary to IE, UL101a, UL84a, UL70a, UL70b, or HCV1, or with pfa, were infected with HCMV (MOI=0.05), incubated for 5 days, and then stained for viral UL44 protein.
Figure 9:
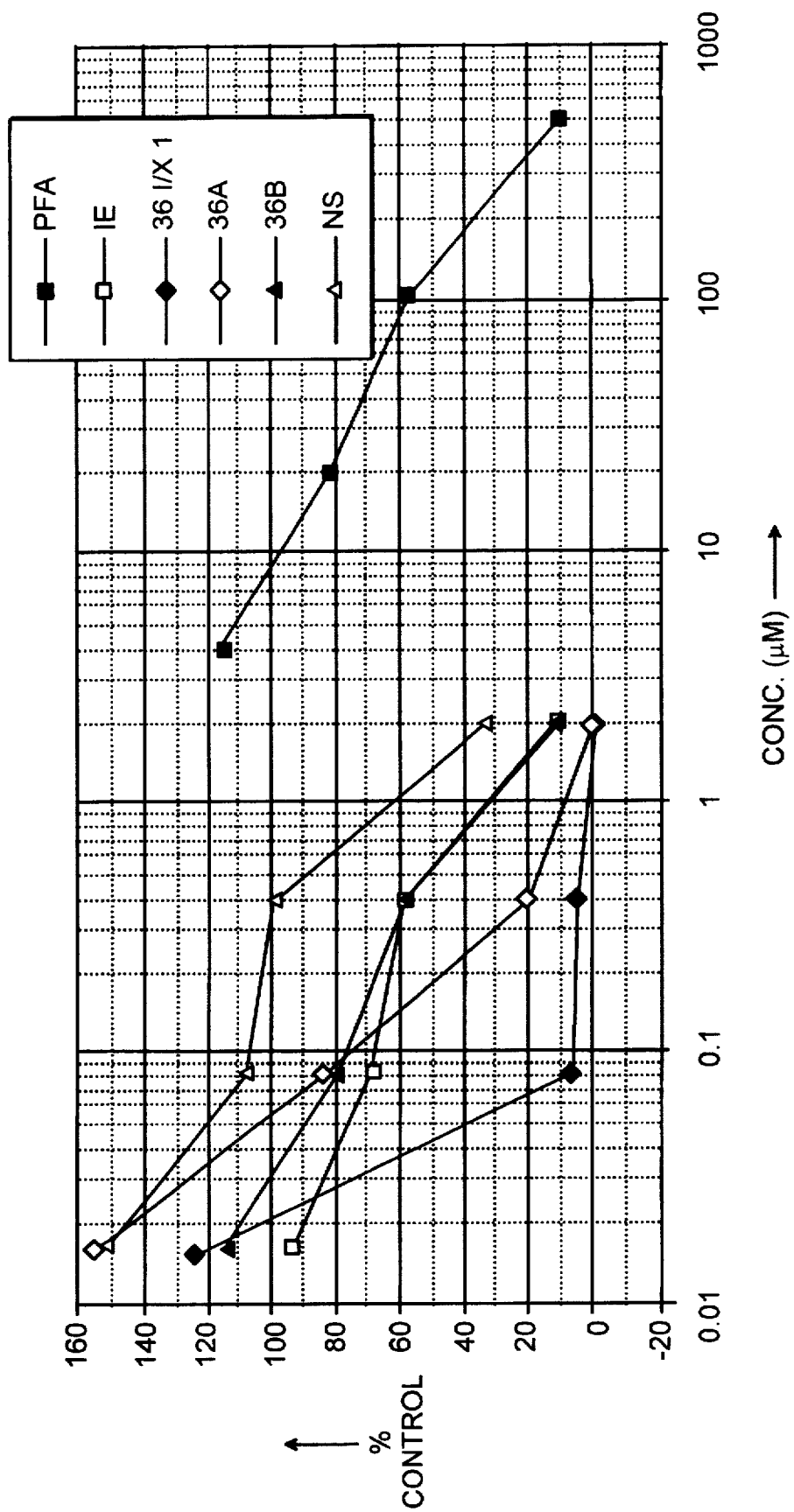
FIG. 9 is a graphic representation of the results of an ELISA in which cells preincubated with oligonucleotides complementary to IE, UL36 I/X 1, UL36A (UL36 I/X 1A), UL36B (UL36 I/X 1B, an intron/exon boundary other than the ones to which UL36 I/X 1, I/X 1A, and I/X 1C are directed), or NS, or with pfa, were infected with HCMV (MOI =0.1), incubated for 5 days, and then stained for viral UL44 protein.
Figure 10:
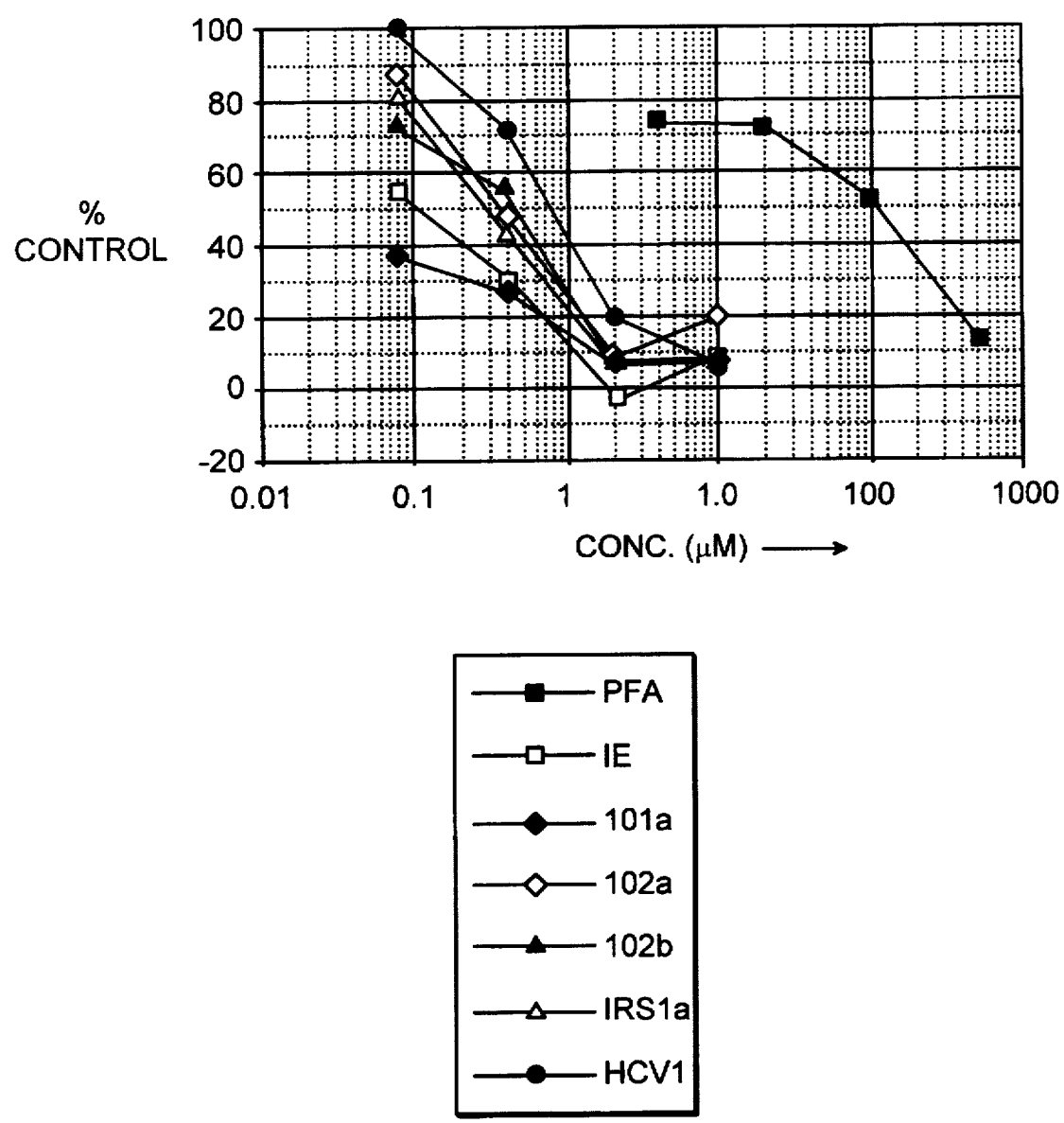
FIG. 10 is a graphic representation of the results of an ELISA in which cells preincubated with oligonucleotides complementary to IE, UL101a, UL102a, UL102b, irsla, or HCV1, or with pfa, were infected with HCMV (MOI=0.05 ), incubated for 6 days, and then stained for viral UL44 protein.

The results shown in FIGS. 7, 8 and 10 demonstrate that UL101a, an oligonucleotide having a nucleotide sequence set forth in the Sequence Listing as SEQ ID NO:5 and directed to the UL101x gene also has inhibitory abilities.

Figure 12:
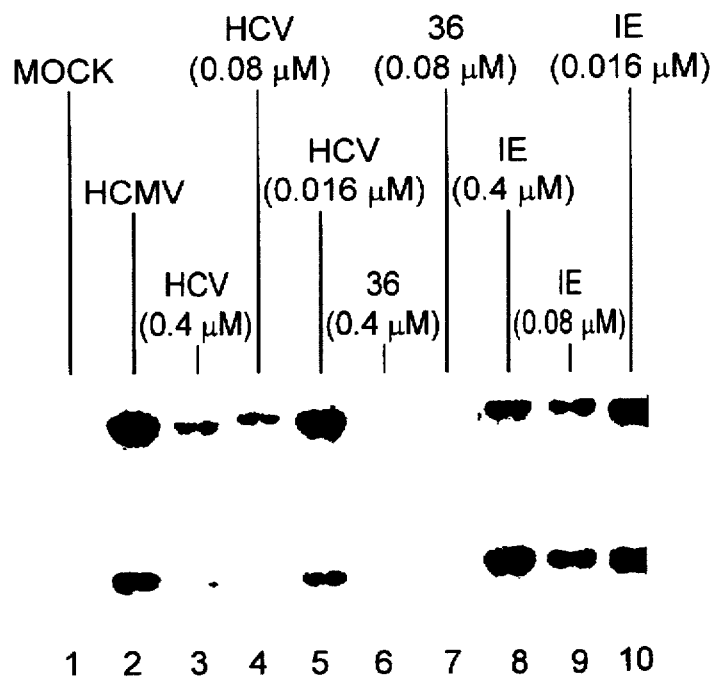
FIG. 12 is a Southern blot showing the relative amount of HCMV replication (using oriLyt as the probe) in cells treated with varying concentration of the oligonucleotides indicated before viral infection at MOI=0.1.
Figure 13:
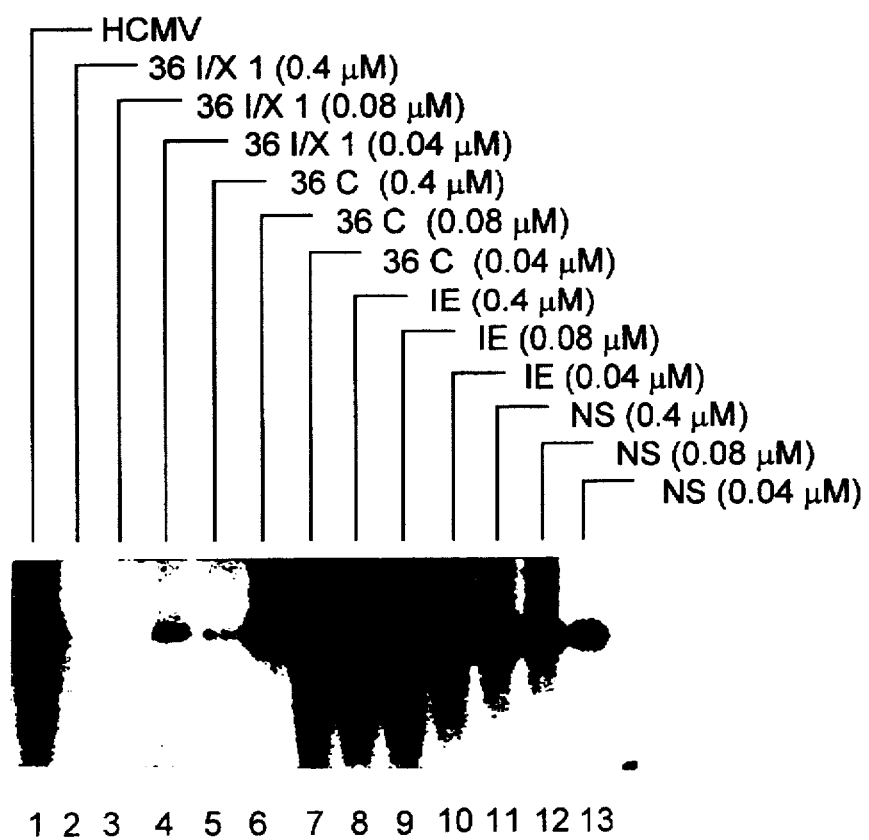
FIG. 13 is a Southern blot showing the relative amount of HCMV replication in cells treated with varying concentration of the oligonucleotides indicated before viral infection at MOI=0.4.

In order to determine whether HCMV DNA synthesis has been inhibited by the oligonucleotides of the invention, Southern blots were prepared from cells pretreated with the oligonucleotides and then infected with HCMV and probed using a $^{32}$P-random primer-generated oriLyt (HCMV origin of replication PvuI-KpnI fragment) probe. Representative autoradiograms of such blots are shown in FIGS. 12 and 13. These results, like those from the ELISA studies, reveal that HCMV DNA replication is reduced to negligible amounts when cells are treated with oligonucleotides complementary to UL36 DNA or RNA at concentrations as low as 0.08 µM. The oligonucleotide directed to the IE2 gene (SEQ ID NO:24) inhibits HCMV DNA replication to a much lesser extent at any concentration than does any of the UL36 oligonucleotides. Furthermore, at certain concentrations, the oligonucleotides of the invention directed to the UL84, and UL101x genes inhibit HCMV DNA replication to a greater extent than does IE, the oligonucleotide directed to the IE2 gene (Azad et al. (1993) *Antimicrobial Agents and Chemother.* 37:1945–1954).

Figure 14:
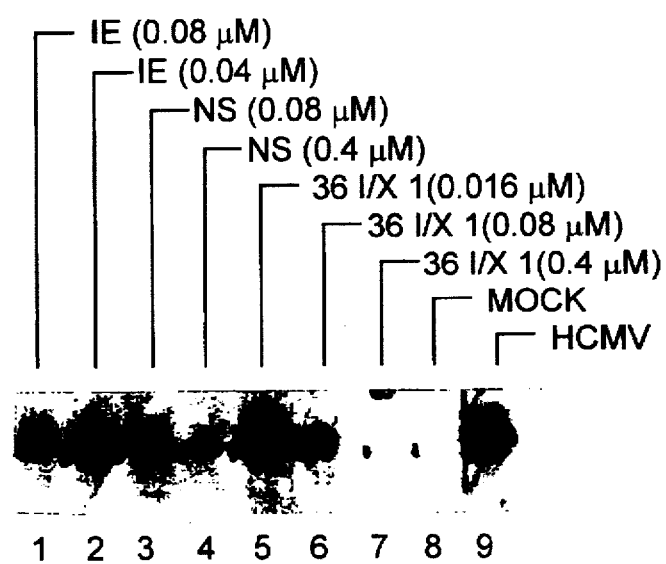
FIG. 14 is a Northern blot showing viral RNA expression in cells treated with varying concentrations of the oligonucleotides indicated before HCMV infection at MOI =0.1. The probe used hybridizes to the UL36 transcript.

Northern blots were also prepared to determine the effect of the oligonucleotides of the invention on HCMV RNA transcription. Total cellular RNA was isolated from cells treated with oligonucleotides and infected (or uninfected, or untreated and infected) at an MOI of 0.1. The blot was probed with a probe that hybridizes to the UL36 transcript. As can be seen in FIG. 14, the UL36 transcript was not detectable at an oligonucleotide concentration of 0.4 µM and is significantly reduced at 0.08 µM, whereas the transcript was detectible at both of these concentrations of IE oligonucleotide.

The results described above confirm that the oligonucleotides of the invention are useful as inhibitors of HCMV-specific products.

That the oligonucleotides of the invention are not toxic to the cells is determined by comparing the rate of $^3$H-thymidine incorporation into the newly synthesized DNA of oligonucleotide-treated cells and untreated cells. Alternatively, cytotoxicity of oligonucleotides under antiviral assay conditions can be evaluated with modified MTT or neutral red assays (Azad et al. (1993) *Antimicrob. Ag. and Chemother.* 37:1945–1954; Babich et al. (1991) *Appl. Environ, Microbiol.* 57:2101–2103; Denzoit et al. (1986) *J. Immunol.* 89:271–277).

The oligonucleotides of the invention are also useful as tools to define gene function, and hence to identify essential genes (e.g., those required for DNA replication), by selective antisense downregulation of a gene of choice. Because HCMV has a long reproductive cycle, DNA replication does not occur until approximately 36 hours post infection (PI), in contrast to herpes simplex virus (HSV) where this event occurs as early as 6–8 hours PI. Similar to HSV however, IE genes are expressed as early as 2 hours PI. This long lag time between the expression of IE genes and the onset of DNA replication characteristic of CMV, makes it very difficult to select temperature sensitive mutants having mutations within essential HCMV genes. In addition, the fact that HCMV productively infects only normal diploid human fibroblasts, eliminates the possibility of creating transfected cell lines that can support virus growth and express essential HCMV genes.

In the antisense approach, a specific viral gene or gene transcript can be disabled or downregulated, by the application of the antisense oligonucleotides of the invention. For example, inhibition of the synthesis and expression of an IE gene product eliminates the function of that IE product. This can be accomplished by administering to a CMV infected cell an antisense oligonucleotide complementary to the UL36, UL84, or UL101x CMV gene which hybridize to the gene or gene transcript, thereby producing the epigenetic equivalent of a mutant CMV deficient in an essential gene. These "antisense mutants" will behave as wild type, except that the essential gene function will have been eliminated or significantly down regulated. In this way, the oligonucleotides of the invention act as "genetic" tools to assess viral factors and their role in the infected cell, and to determine how gene expression regulates HCMV DNA replication.

The oligonucleotides of the invention are also useful as diagnostic probes. Because these oligonucleotides are capable of inhibiting viral replication, they are useful in a diagnostic assay that confirms the presence of HCMV in clinical or experimental samples. The samples are incubated with untreated or oligonucleotide-pretreated cells. The inhibition of growth of HCMV in the treated versus the untreated confirms the presence of HCMV in the sample. Such an assay is useful for detecting CMV contamination as well as infection of individuals.

The present invention further provides a therapeutic composition having antiviral activity against HCMV infection. The composition includes at least an oligonucleotide of the present invention, along with a physiologically acceptable carrier.

As used herein, a "physiologically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional meduim or agent is incompatible with the active ingredient, its use in the therapeutic compositions is contemplated. Supplementary active ingredients can also be incorporated into the compositions.

The oligonucleotides of the invention may also be used to treat HCMV infection in humans. In this method, the pharmaceutical composition is administered once in a therapeutically effective amount or repeatedly in less than therapeutic amounts. Administration may be by intravenous or intraperitoneal injection, or by intranasal, oral, transdermal, or subcutaneous administration. Effective dosages of the oligonucleotides and modes of their administration in the treatment of HCMV can be determined by routine experimentation. The pharmaceutical forms suitable for injectable or other use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

The patent and scientific literature referred to herein establishes the knowledge that is available to those with skill in the art. The issued U.S. patents, allowed applications, and other publications cited herein are hereby incorporated by reference.

The following examples illustrate the preferred modes of making and practicing the present invention, but are not meant to limit the scope of the invention since alternative methods may be utilized to obtain similar results.

EXAMPLES

1. Synthesis of Oligonucleotides

Unmodified (phosphodiester-linked) oligodeoxyribonucleotides, oligoribonucleotides, and DNA/RNA oligonucleotide chimeras are synthesized on an automated DNA synthesizer (Applied Biosystems, Foster City, Calif.) using standard H-phosphonate chemistry as described in U.S. Pat. No. 5,149,789, or using standard phosphoramidite chemistry as described in Uhlmann et al. (*Chem. Rev.* (1990) 90:534–583). Oligonucleotide phosphorothioates are also synthesized using the H-phosphonate approach described in U.S. Pat. No. 5,149,789. Oligonucleotides with at least one nonphosphodiester internucleotide linkage including a phosphoramidite and/or methylphosphonate linkage at preselected positions are prepared using the procedures described in Agrawal and Goodchild (*Tetrahedron Lett.* (1987) 28:3539–3542); Agrawal et al. (*Proc. Natl. Acad. Sci.* (U.S.A) (1988) 85:7079–7083); and/or Uhlmann et al. (*Chem. Rev.* (1990) 90:534–583). Oligonucleotides having at least one phosphorodithioate, carbamate, phosphate esters, alkylphosphonates, alkylphosphonothioates, phosphosphoramidates, carbonates, phosphate triesters, acetamidate, and carboxymethyl esters are prepared as described in Uhlmann et al. (*Chem. Rev.* (1990) 90:534–583).

2. ELISA for Measuring Inhibition of HCMV Replication

The oligonucleotides of the invention complementary to HCMV RNA (TABLE 1) and other were tested for antiviral activity by ELISA. Human foreskin fibroblasts (HFF) cells taken from explants were seeded in a 96 well plate at $5 \times 10^3$ cells per well in Dulbeccos Modified Eagles Medium (DMEM) (Mediatech, Washington, D.C.) supplemented with 10% (vol/vol) fetal calf serum. 24 hours after seeding, cells were washed once with Opti-MEM (Gibco-BRL, Gaithersburg, Md.). Then, various concentrations of antisense oligonucleotides were added in Opti-MEM. Cells were allowed to incubate with oligonucleotides for about 16 hours (overnight). The medium was then removed and cells were washed three times with Opti-MEM. Then, the cells were infected with HCMV (strain AD169) (American Type Culture Collection, Rockville, Md.; ATCC VR-538) at an MOI of 0.05–0.4. This HCMV strain was maintained as frozen stocks. Virus was adsorbed for 1 hour before cells were washed and the medium replaced with Opti-MEM containing oligonucleotides.

Five to six days post infection (PI), cells were fixed (100% ethanol) and reacted with primary antibody specific for polymerase accessory factor, the UL44 gene product. Cells were then reacted with a secondary antibody (HRP-conjugated goat anti-mouse IgG). The OD at $A_{450}$ as determined using a plate reader.

3. Southern Blot Analysis

HFF cells were seeded in 6 cm dishes at a density of $2\times10^5$ cells per dish and treated exactly as described above, except that oligonucleotide was added at only one concentration (0.4 μM). At five days total cellular DNA was extracted from treated cells directly on the 6 cm dish with 400 μl of 2% SDS, 10 mM Tris-HCl, pH 8.0, 10 mM EDTA. The lysates were then transferred to a 1.5 ml microcentrifuge tube where 200 μg/ml proteinase K (Boehringer Mannheim, Indianapolis, Ind.) was added. The tubes were incubated at 50° C. for one hour. 40 μl 3.0M sodium acetate were added to the lysates. The lysates were extracted once with phenol/chloroform/isoamyl alcohol (25:24:1). The aqueous phase was transferred to a fresh tube and extracted once with chloroform/isoamyl (24:1) after which the aqueous phase was again transferred to a fresh tube and 2 volumes of 100% ethanol was added. DNA was pelleted at 14,000×g, resuspended in 50 μl of TE (10 mM Tris-HCl, pH 8.0, 1 mM EDTA). Ten microliters of DNA was treated with 25 U of EcoRI (New England BioLabs, Beverly, Mass.) in a volume of 50 μl at 37° C. for 4–16 hours, subjected to electrophoresis through a 0.8% agarose gel, and transferred to Zeta-probe nylon membrane (Bio-Rad, Richmond, Calif.), using the alkaline transfer method according to manufacturer's instructions. Hybridizations were carried out using a 32P-random primer-generated oriLyt (HCMV origin of replication PvuI-KomI fragment) probe with an approximate specific activity of $1\times10^9$ cpm/μg. Filters were hybridized with 5 ng of probe in 10 ml of hybridization buffer (1.5×SSPE, 7% SDS (w/v), 10% PEG (weight:volume)) for 16 hours at 68° C. in a hybridization oven (Robbins Scientific, (Sunnyvale, Calif.). Post-hybridization washes were performed with 2×SSC, 0.1% SDS (weight:volume) for 2×15 minutes at room temperature followed by 0.1×SSC, 0.1% SDS (weight:volume) twice for 45 minutes at 68° C. Southern blots were then exposed to X-OMAT AR (Kodak, Rochester, N.Y.) X-ray film at −80° C. for 24 hours.

4. Northern Blot Analysis

Treated cells were lysed directly on a 6 cm dish with 500 μl of 2% SDS, 200 mM Tris-HCl, pH 7.5, 1 mM EDTA. Lysates were transferred to a 1.5 ml microcentrifuge tube and 150 μl of ice cold precipitation buffer (42.9 g potassium acetate, 11.2 ml acetic acid and water to 100 ml) was added. Tubes were vortexed and iced for 2 minutes, centrifuged for 5 minutes (room temperature). Supernatants were transferred to fresh tubes and extracted twice with 300 μl of chloroform/isoamyl alcohol (24:1). RNA was precipitated with 0.65 ml of ice-cold isopropanol and pelleted for 5 minutes at 14,000×g. Pelleted RNA was resuspended in 50 μl of 100% formamide.

10 μg (approximately 10 μl) of RNA was electrophoresed on a 10% agarose gel containing 6% formaldehyde and then transferred to Zeta-probe nylon membrane. The filter was hybridized with a RNA probe (ribobrobe) to the UL36 transcript (SalI BssHII 672 bp probe within the UL36 transcript) in hybridization buffer (1.5×SSPE, 1% SDS, 50% formamide, 0.5% non-fat dried milk and 100 μg per ml denatured salmon sperm DNA) at 65° C. for 16 hours. Blots were then washed with 2×SSC, 0.1% SDS (weight:volume) for 2×15 minutes at room temperature followed by 0.1×SSC, 0.1% SDS (weight:volume) twice for 45 minutes at 65° C. Southern blots were then exposed to X-OMAT AR (Kodak) X-ray film at −80° C. for 24 hours.

5. Cytotoxicity Assays

Cytotoxicity of oligonucleotides under antiviral assay conditions is evaluated with modified MTT or neutral red assays (Azad et al. (1993) *Antimicrob. Ag. and Chemother.* 37:1945–1954; Babich et al. (1991) Appl. Environ, Microbiol. 57:2101–2103; Denzoit et al. (1986) *J. Immunol.* 89:271–277). HFF cells are treated exactly as described above for the 96-well ELISA immunoassay, including the oligonucleotide pretreatment. Instead of virus infection, cells are mock inoculated with sterile medium only. At the end of the incubation period (4 days of oligonucleotide treatment), 10 μl of MTT (5 mg/ml in PBS) is added directly to the culture medium of each well (100 μl) and cells are incubated for an additional 2 hours. Medium is then removed from each well, and insoluble blue formazan product is dissolved in acidified isopropanol. The optical density at 540 nm is determined with a BioTex model EL312c microplate reader. Means of triplicate assays are expressed as the percentage of signal resulting from sham-treated cells. A minimal background from wells containing no cells is subtracted prior to any calculations.

Cytotoxicity of the oligonucleotides can also be determined by comparing the incorporation of $^3$H-thymidine into cells that have been pretreated with the oligonucleotides of the invention for 24 hours with those cells that have been untreated. The cells are then pulsed with 1 μCi of $^3$H-thymidine (NEN/DuPont) for 4 hours at 37° C. After brief cell lysis with 0.4M NaOH, the lysates are placed on fiberglass filtermats and washed extensively. The dried filters are transferred to scintillation vials containing 3 ml of scintillant and counted.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A synthetic oligonucleotide which binds specifically to an mRNA encoding the UL36, UL84, UL101x-102, or UL112-113 genes of a human cytomegalovirus, the oligonucleotide binding to a portion of the mRNA which is complementary to SEQ. ID. NOS: 1, 2, 3, 4, 5, 6, 7, 8, or 9, wherein the binding inhibits cytomegalovirus replication.

2. The oligonucleotide of claim 1 further comprising at least one modified internucleoside linkage, at least modified sugar moiety, or at least one modified internucleoside linkage and at least one modified sugar moiety.

3. The oligonucleotide of claim 2 wherein the modified internucleoside linkage is selected from the group consisting of phosphorothioate, alkylphosphonate, and combinations thereof.

4. The modified oligonucleotide of claim 2 wherein the modified sugar moiety comprises a 2'-O-methyl group.

5. The oligonucleotide of claim 1 which is about 15-30 nucleotides in length.

6. The oligonucleotide of claim 1 which comprises at least one deoxyribonucleotide.

7. The oligonucleotide of claim 1 which comprises at least one ribonucleotide.

8. The oligonucleotide of claim 7 further comprising at least one 2'-O-methyl group.

9. The oligonucleotide of claim 6 which comprises at least one ribonucleotide.

10. The oligonucleotide of claim 9 further comprising at least one 2'-O-methyl group.

11. The oligonucleotide of claim 1 which hybridizes to an intron/exon boundary of UL36.

12. The oligonucleotide of claim 11 consisting of the nucleic acid sequence set forth in Sequence Listing as SEQ ID NO:1, SEQ ID NO:2, or SEQ ID NO:3.

13. The oligonucleotide of claim 1 which hybridizes to the putative translational start region of UL84.

14. The oligonucleotide of claim 13 consisting of the nucleic acid sequence set forth in the Sequence Listing as SEQ ID NO:4, or SEQ ID NO:5.

15. The oligonucleotide of claim 1 which hybridizes to the putative translational start region of UL101x.

16. The oligonucleotide of claim 15 consisting of the nucleic acid sequence set forth in the Sequence Listing as SEQ ID NO:6.

17. The oligonucleotide of claim 1 which hybridizes to an intron/exon boundary of UL112-113.

18. The oligonucleotide of claim 17 consisting of the nucleic acid sequence set forth in the Sequence Listing as SEQ ID NO:7, SEQ ID NO:8, or SEQ ID NO:9.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

TGGGGCTTAC CTTGCGAACA                     20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:2:

GACGTGGGGC TTACCTTGCG                     20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:3:

TCTTCAACGA CGTGGGGCTT                     20

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:4:

GACGCGTGGC ATGCTTGGTG T                   21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:5:

AGGTTGGGGT CGACGCGTGG C 21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:6:

GGCTGAGCGG TCATCCTCGG A 21

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:7:

CGGGACTCAC CGTCGTTCTG 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:8:

GGAGGAGAGC CTACAGACGG 20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:9:

AGTAACGCAC CGTCGGTGCC 20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:10:

CAACGACGTG GGGCTTACCT                    20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:11:

ACCCCTGCTT ACTGGTGAGA                    20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:12:

GTTGTTTTTA CCTGAAACCC                    20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:13:

CCGAACGGCG GTTTCTCCAC                    20

( 2 ) INFORMATION FOR SEQ ID NO:14:

```
       ( i ) SEQUENCE CHARACTERISTICS:
               ( A ) LENGTH: 21 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:14:
```

CTTGCGATCC ATCCCGGACA G                                            21

( 2 ) INFORMATION FOR SEQ ID NO:15:

```
       ( i ) SEQUENCE CHARACTERISTICS:
               ( A ) LENGTH: 20 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:15:
```

CTCCGAGAGG CGCGTCTTGC                                              20

( 2 ) INFORMATION FOR SEQ ID NO:16:

```
       ( i ) SEQUENCE CHARACTERISTICS:
               ( A ) LENGTH: 22 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:16:
```

ACGAGCGTCA TCGTCGCGCC GG                                           22

( 2 ) INFORMATION FOR SEQ ID NO:17:

```
       ( i ) SEQUENCE CHARACTERISTICS:
               ( A ) LENGTH: 22 base pairs
               ( B ) TYPE: nucleic acid
               ( C ) STRANDEDNESS: single
               ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:17:
```

CATCGTCGCG CCGGCACGAT GC                                           22

( 2 ) INFORMATION FOR SEQ ID NO:18:

```
       ( i ) SEQUENCE CHARACTERISTICS:
               ( A ) LENGTH: 21 base pairs
               ( B ) TYPE: nucleic acid
               ( C ) STRANDEDNESS: single
```

(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:18:

GCGAAACGAC ATGGCCAAAT C                                         21

(2) INFORMATION FOR SEQ ID NO:19:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:19:

GCGCGTGGGT GCCATACTCT T                                         21

(2) INFORMATION FOR SEQ ID NO:20:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:20:

CCGTTGCGCT GGGCCATGGG                                           20

(2) INFORMATION FOR SEQ ID NO:21:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:21:

CATGGGCGCC GGACACCTGC                                           20

(2) INFORMATION FOR SEQ ID NO:22:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA ( i i i ) HYPOTHETICAL: NO ( i v ) ANTI-SENSE: YES ( x i ) SEQUENCE DESCRIPTION: SEQ ID NO:22:

AAATCATCTC TGACGTAGCG                                                      20

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:23:

GCTCGCTACG CTCGCTACGT C                                                    21

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:24:

GCGTTTGCTC TTCTTCTTGC G                                                    21